(12) United States Patent
Chen et al.

(10) Patent No.: US 7,206,375 B2
(45) Date of Patent: Apr. 17, 2007

(54) METHOD AND APPARATUS FOR IMPLEMENT XANES ANALYSIS

(75) Inventors: Zewu Chen, Schenectady, NY (US); Walter Gibson, Voorheesville, NY (US)

(73) Assignee: X-Ray Optical Systems, Inc., East Greenbush, NY (US)

(*) Notice: Subject to any disclaimer, the term of this patent is extended or adjusted under 35 U.S.C. 154(b) by 0 days.

(21) Appl. No.: 11/291,349

(22) Filed: Dec. 1, 2005

(65) Prior Publication Data

US 2006/0120508 A1     Jun. 8, 2006

Related U.S. Application Data

(63) Continuation of application No. PCT/US04/17454, filed on Jun. 2, 2004.

(60) Provisional application No. 60/475,148, filed on Jun. 2, 2003.

(51) Int. Cl.
*G01F 23/06* (2006.01)

(52) U.S. Cl. .............................. 378/51; 378/53; 378/84

(58) Field of Classification Search ............ 378/50–56, 378/70–73, 82–87
See application file for complete search history.

(56) References Cited

U.S. PATENT DOCUMENTS

| 4,642,811 A | 2/1987 | Georgopoulos ............... 378/53 |
| 2002/0131550 A1* | 9/2002 | Fujioka et al. ................. 378/44 |

FOREIGN PATENT DOCUMENTS

| JP | 06 313757 A | 11/1994 |
| JP | 2001 021507 A | 1/2001 |

OTHER PUBLICATIONS

Z. Chen et al., "Microanalysis by Monochromatic Microprobe X-Ray Fluorescence-Physical Basis, Properties, and Future Prospects", Journal of Applied Physics, American Institute of Physics, vol. 84, No. 2, pp. 1064-1073 (Jul. 15, 1998).
Z. Chen et al., "Microprobe X-Ray Fluorescence With the Use of Point-Focusing Diffractors", Applied Physics Letters, American Institute of Physics, vol. 71, No. 13, pp. 1884-1886 (Sep. 29, 1997).

* cited by examiner

*Primary Examiner*—Edward J. Glick
*Assistant Examiner*—Irakli Kiknadze
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

Compact, low-power-consuming systems and methods for exposing samples to high-energy radiation, for example, for exposing samples to x-rays for implementing x-ray absorption near edge analysis (XANES). The systems and methods include a low-power-consuming radiation source, such as an x-ray tube; one or more tunable crystal optics for directing and varying the energy of the radiation onto a sample under analysis; and a radiation detecting device, such as an x-ray detector, for detecting radiation emitted by the sample. The one or more tunable crystal optics may be doubly-curved crystal optics. The components of the system may be arranged in a collinear fashion. The disclosed systems and methods are particularly applicable to XANES analysis, for example, XANES analysis of the chemical state of chromium or another transition metal in biological processes.

31 Claims, 7 Drawing Sheets

METHOD AND APPARATUS FOR IMPLEMENT XANES ANALYSIS

CROSS-REFERENCE TO RELATED APPLICATIONS

This application is a continuation of PCT Application PCT/US2004/017454, filed Jun. 2, 2004, and published under the PCT Articles in English as WO 2004/111624 A2 on Dec. 23, 2004. PCT/US2004/017454 claimed priority to U.S. Provisional Application No. 60/475,148, filed Jun. 2, 2003. The entire disclosures of PCT/US2004/017454 and U.S. Ser. No. 60/475,148 are incorporated herein by reference in their entirety. In addition, this application contains subject matter which is related to the subject matter of the following application, which is hereby incorporated herein by reference in its entirety:

"An Optical Device for Directing X-rays having a Plurality of Optical Crystals" by Chen, U.S. Ser. No. 60/400,809, filed Aug. 2, 2002.

STATEMENT REGARDING GOVERNMENT RIGHTS

This invention was made with U.S. Government support under Grant 5R44CA088678-03 awarded by the National Institutes of Health. Accordingly, the U.S. Government has certain rights in the invention.

TECHNICAL FIELD

This invention relates generally to apparatus and methods used for x-ray analysis of samples to determine their chemical content. Specifically, the present invention provides improved methods and apparatus for x-ray absorption near-edge structure analysis.

BACKGROUND OF THE INVENTION

X-ray absorption spectroscopy is an attractive technique for chemical analysis, for example, chemical oxidation state analysis. See, for example, McBreen, et al. "In situ time-resolved x-ray absorption near edge structure study of the nickel oxide electrode", *J. Phys. Chem.* 93, 6308 (1989) and Shimizugawa, et al., "X-ray absorption fine structure of samarium-doped borate glasses", *J. Appl. Phys.* 81, 6657 (1997), the disclosures of which are incorporated by reference herein. One specific form of x-ray absorption spectroscopy is X-ray absorption near-edge structure analysis, which is commonly referred to by its acronym "XANES" analysis. XANES analysis is a powerful, non-destructive technique for examining the chemical state of an element, for example, for examining the oxidation state of an element. Specifically, XANES analysis is an x-ray absorption spectroscopy technique in which the x-ray absorption coefficient of a sample is measured as a function of photon energy near the threshold of an absorption edge.

In a XANES measurement, the position of the x-ray absorption edge changes with oxidation state due to changes in the energy required to promote 1 s electrons to the continuum. In addition, fine structure both before and after the absorption edge can be used to measure details of the chemical structure of the absorbing element. For minor or trace constituents, details of the absorption edge can be determined by measuring the intensity of the characteristic x-ray fluorescence signal for that element as a function of the energy of the exciting x-ray beam in the region of the absorption edge.

The pre-edge region, or the region immediately below the absorption edge, contains valuable bonding information and the edge position contains information about the charge on the absorber. One characteristic of an absorber that can be determined by XANES is its oxidation state. For instance, the oxidation state of an absorber can be determined from the precise energy of the x-ray absorption edge and pre-edge features.

XANES analysis provides an effective method of determining the oxidation state of an element, for example, the oxidation states of chromium. For example, the K-edge XANES spectrum of $[CrO4]^{2-}$ is characterized by an intense pre-edge peak (see Bajt, et al., "Synchrotron X-ray Microprobe Determination of Chromate Content Using X-ray Absorption Near-Edge Structure", *Anal. Chem.* 65, 1800–1804 (1993), the disclosure of which is incorporated by reference herein). Bajt, et al. demonstrated that quantitative analysis of trace level Cr(VI) can be achieved with the XANES technique using a synchrotron radiation source. In a recent study (see Dillon, et al. "Microprobe X-ray Absorption Spectroscopic Determination of the Oxidation state of V79 Chinese Hamster Lung Cells to Genotoxic Chromium Complexes", *Chem, Res. Toxicol* 10, 533–535 (1997), the disclosure of which is incorporated by reference herein), the XANES technique performed with a synchrotron source also showed that the Cr oxidation state in animal lung cells can be determined.

Two modes of XANES analysis exist, namely, the transmission mode and the fluorescence mode. In the transmission mode, a XANES spectrum is obtained by measuring the intensity of the x-rays transmitted through a sample as a function of the energy of the incident x-rays, that is, the x-ray photons. In the fluorescence mode, the fluorescence signal of an absorber is measured as a function of the energy of the incident beam. For dilute biological systems, for example, the fluorescence method removes the 'background' absorption due to other constituents, thereby improving the sensitivity by orders of magnitude.

A major limitation of the application of the XANES technique has been that such measurements have only been carried out at synchrotron facilities where x-ray beams of the required intensity and bandwidth have been available. In many applications it is also desirable to have good spatial resolution since, for heterogeneous samples spot analysis on as small a scale as possible is crucial. Typically, the XANES technique requires an intense, monochromatic x-ray beam. In addition, in order to obtain the desired x-ray energy near the absorption edge of the absorption spectrum of a substance, it is preferred that the x-ray beam used in a XANES system also be tunable, that is, the energy of the beam is preferably variable and controllable. To obtain a tunable, monochromatic x-ray photons, a white x-ray source coupled with an x-ray monochromator is typically necessary. Conventional laboratory x-ray sources have very low conversion efficiency for continuum x-ray generation, that is, conventional laboratory x-rays sources are simply not bright enough. Conventional laboratory x-ray sources are also divergent and typically suffer intensity losses imposed by the inverse square law. Due to the low brightness and divergent nature of laboratory sources, many important applications of XANES must be done with a synchrotron radiation source that provides an intense, polarized white x-ray beam. However, the high cost, limited time of use, and typically remote nature of synchrotron sources are not suitable for routine laboratory analysis. Thus, there is a need in the art to provide an affordable, compact XANES analysis system for performing real-time chemical analysis, for example, real-time oxidation state determination.

Recent innovations in doubly-bent crystal fabrication technology makes the precise two-dimensional bending of crystal planes possible (see, for example, U.S. Pat. No. 6,285,506, issued Sep. 4, 2001, entitled "Curved Optical Device and Method of Fabrication", which is hereby incorporated by reference herein). Doubly-curved crystals collect a large solid angle of x-ray photons from a diverging x-ray source and focus them to a relatively small spot with a narrow energy bandwidth. A high performance doubly-curved crystal can provide an intense monochromatic micro x-ray beam (see Chen, et al., "Microprobe X-ray Fluorescence with the Use of Point-focusing Diffractors", *Applied Physics Letters,* 71 (13), 1884 (1997), the disclosure of which is incorporated by reference herein). The energy of the beam can be tuned within a certain range by scanning the crystal optic. Crystal optics provide high intensity gain and narrow energy bandwidth and are thus ideally suited for use in XANES analysis, for example, one aspect of the present invention employs a crystal optic, for instance, a doubly-curved, toroidal crystal optic, for directing and focusing x-rays in a XANES analysis system.

There are two principal types of focusing geometries for x-ray crystal optics, namely, the Johann geometry and the Johansson geometry. Three-dimensional point-to-point focusing geometries are obtained by rotating the Johann or Johansson geometry about the source-image line. The Johansson-type point-focusing geometry is free of geometrical aberration and provides a larger solid collection angle than the Johann type. But the Johansson geometry is very difficult to achieve in practice.

SUMMARY OF THE INVENTION

A compact, high sensitivity, low power and low cost, table-top instrument for implementing XANES measurements will make possible chemical speciation and characterization studies in a broad variety of applications in medicine, science and industry. The present invention provides methods and apparatus for performing XANES analysis which address many of the limitations of prior art methods and apparatus. For example, one aspect of the invention is a system for performing x-ray absorption near-edge structure analysis, the system comprising: means for directing x-rays having a first energy onto a sample; means for detecting x-rays having a second energy emitted by the sample when the sample is exposed to x-rays; and means for varying the first energy of the x-rays directed onto the sample wherein the second energy of the x-rays emitted by the sample varies responsive thereto and wherein information concerning near-edge structure of an x-ray absorption spectrum of the sample can be obtained by analysis in part of the variation in the second energy of the detected x-rays. In one aspect of the invention, the means for directing x-rays comprises an x-ray optic. Due to the high intensity gain and narrow energy bandwidth that can be achieved with a crystal x-ray optic, for example, a toroidal crystal optic, in one aspect of the present invention, the x-ray optic used is a crystal x-ray optic. In another aspect of the invention, the x-ray optic comprises a tunable x-ray optic and wherein the means for varying the first energy of the x-rays directed on the sample comprises means for tuning the tunable x-ray optic, for example, θ-2θ tuning, x-x tuning, or x-2x tuning.

Another aspect of the invention comprises a method of practicing x-ray absorption near-edge structure analysis, the method comprising: directing x-rays having a first energy onto a sample; detecting x-rays having a second energy emitted by the sample when the sample is exposed to x-rays; varying the first energy of the x-rays directed onto the sample wherein the second energy of the x-rays emitted by the sample varies responsive thereto; and analyzing the variation in the second energy of the detected x-rays to provide information concerning near-edge structure of an x-ray absorption spectrum of the sample. In one aspect of this invention, directing x-rays having a first energy comprises diffracting x-rays with a tunable x-ray optic and wherein varying the first energy of the x-rays comprises tuning the x-ray optic, for example, by θ-2θ tuning, x-x tuning, or x-2x tuning. For example, in one aspect of the invention, the tunable x-ray optic has an axis, and tuning the x-ray optic comprises rotating the tunable x-ray optic about the axis.

Another aspect of the present invention is a device for directing x-rays, the device comprising an x-ray optic having an azimuthal angle greater than about 90 degrees. In one aspect of the invention, the azimuthal angel of the optic is greater than about 120 degrees, for example, about 360 degrees. In one aspect of the invention, the x-ray optic comprises at least one doubly-curved crystal optic. In another aspect of the invention, the doubly-curved crystal optic comprises a plurality of doubly-curved optical crystals.

Another aspect of the invention is a doubly-curved crystal optic for focusing x-rays having a predetermined focusing energy, the crystal optic comprising a silicon crystal having 311 diffraction planes; wherein the silicon crystal comprises: a major bending diameter (2R) of about 220 mm; a minor bending radius (r) of about 90 mm; a focal distance (f) of about 140 mm; and a Bragg angle ($\theta_B$) of about 40 degrees. In one aspect of this invention, the predetermined focusing energy is about 6.0 kilo-electron-Volts.

Another aspect of the present invention is a method for determining the carcinogenicity of an element in a sample, the method comprising: directing x-rays having a first energy onto a sample; detecting x-rays having a second energy emitted by the element when the sample is exposed to x-rays; varying the first energy of the x-rays directed onto the sample wherein the second energy of the x-rays emitted by the element varies responsive thereto; analyzing the variation in the second energy of the detected x-rays to provide information concerning near-edge structure of an x-ray absorption spectrum of the element wherein the oxidation state of the element can be determined; and comparing the oxidation state of the element to known oxidation states for the element to determine the carcinogenicity of the element.

Another aspect of the present invention is a method for monitoring oxidation changes of an element in a cell sample with x-ray absorption near-edge analysis, the method comprising: directing x-rays having a first energy onto an element in a sample; detecting x-rays having a second energy emitted by the element when the element is exposed to x-rays; varying the first energy of the x-rays directed onto the sample wherein the second energy of the x-rays emitted by the element varies responsive thereto; and analyzing the variation in the second energy of the detected x-rays to provide information concerning near-edge structure of an x-ray absorption spectrum of the element wherein the oxidation state of the element can be determined.

Another aspect of the present invention is device for analyzing the chemical state of an element in a sample by x-ray absorption near-edge structure analysis, the device comprising: means for directing x-rays having a first energy onto an element in a sample; means for detecting x-rays having a second energy emitted by the element when the element is exposed to x-rays; means for varying the first energy of the x-rays directed onto the sample wherein the second energy of the x-rays emitted by the element varies responsive thereto and wherein information concerning near-edge structure of an x-ray absorption spectrum of the element can be obtained by analysis in part of the variation in the second energy of the detected x-rays; and means for determining the chemical state of the element from the information concerning the near-edge structure. In one aspect of the invention, the device is used for medical analysis, biological analysis, environmental analysis, environmental monitoring, industrial process control, or material science analysis. For example, in one aspect of the invention, the medical analysis is intracellular analysis, transition metal uptake analysis, oxidative process analysis, or analysis of the oxidative state of metallic genotoxins.

The various aspects of the present invention provide methods and apparatus for practicing XANES analysis that heretofore were impractical, for example, impractical for small research or scientific laboratories and industrial applications. The limited availability and prohibitive cost of typical x-ray sources required in the prior art for performing XANES analysis, for example synchrotron-based systems, limited the practicality of XANES analysis for the smaller laboratory, field use, or industrial use. In addition, prior art XANES analysis are cumbersome to repeatedly adjust for x-ray energy variation and thus require time-consuming re-adjustment or part substitution. In contrast, several aspects of the present invention facilitate the adjustment or variation of x-ray energy and thus expedite the analysis process.

The aspects of the invention described above, as well as other aspects of the present invention and their improvements and benefits over the prior art, will become more apparent upon review of the attached drawings, description below, and attached claims.

BRIEF DESCRIPTION OF THE DRAWINGS

The subject matter which is regarded as the invention is particularly pointed out and distinctly claimed in the concluding portion of the specification. The invention, however, both as to organization and method of practice, together with further objects and advantages thereof, may be best understood by reference to the following detailed description of the preferred embodiment(s) and the accompanying drawings in which:

DETAILED DESCRIPTION OF A PREFERRED EMBODIMENT

Figure 1:
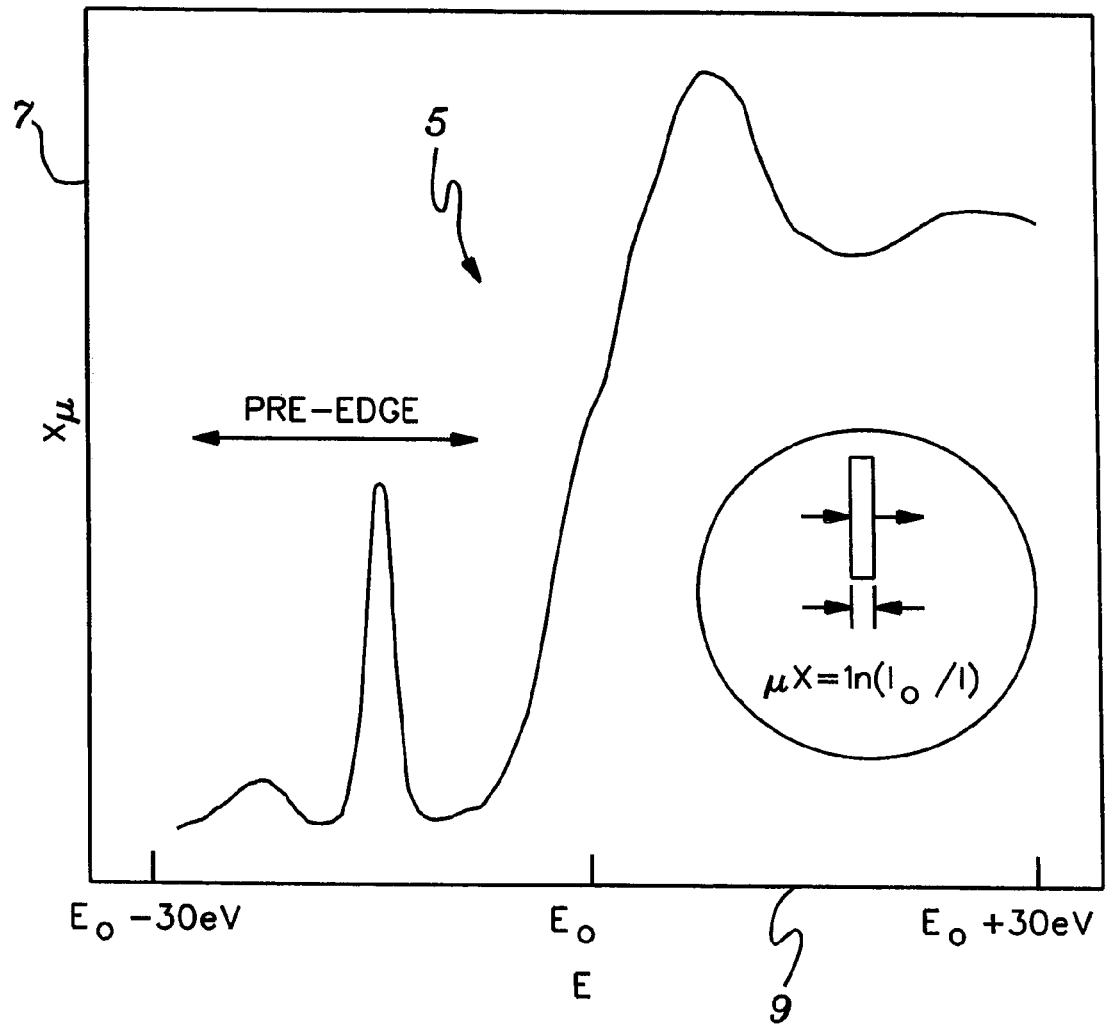
FIG. 1 is a schematic diagram illustrating a typical near-edge x-ray absorption spectrum.

FIG. 1 illustrates a typical XANES spectrum 5 that can be produced using one aspect of the present invention. The ordinate 7 shown in FIG. 1 represents the intensity of the x-ray fluorescence from a sample. The abscissa 9 of FIG. 1 represents the energy in eV of the corresponding x-ray onto the sample under analysis. $E_O$ is the energy of the absorption edge. As shown in FIG. 1, a typical XANES spectrum spans an energy range from about 30 eV below the energy of the absorption edge to about 30 eV above the energy of the absorption edge.

Figure 2:
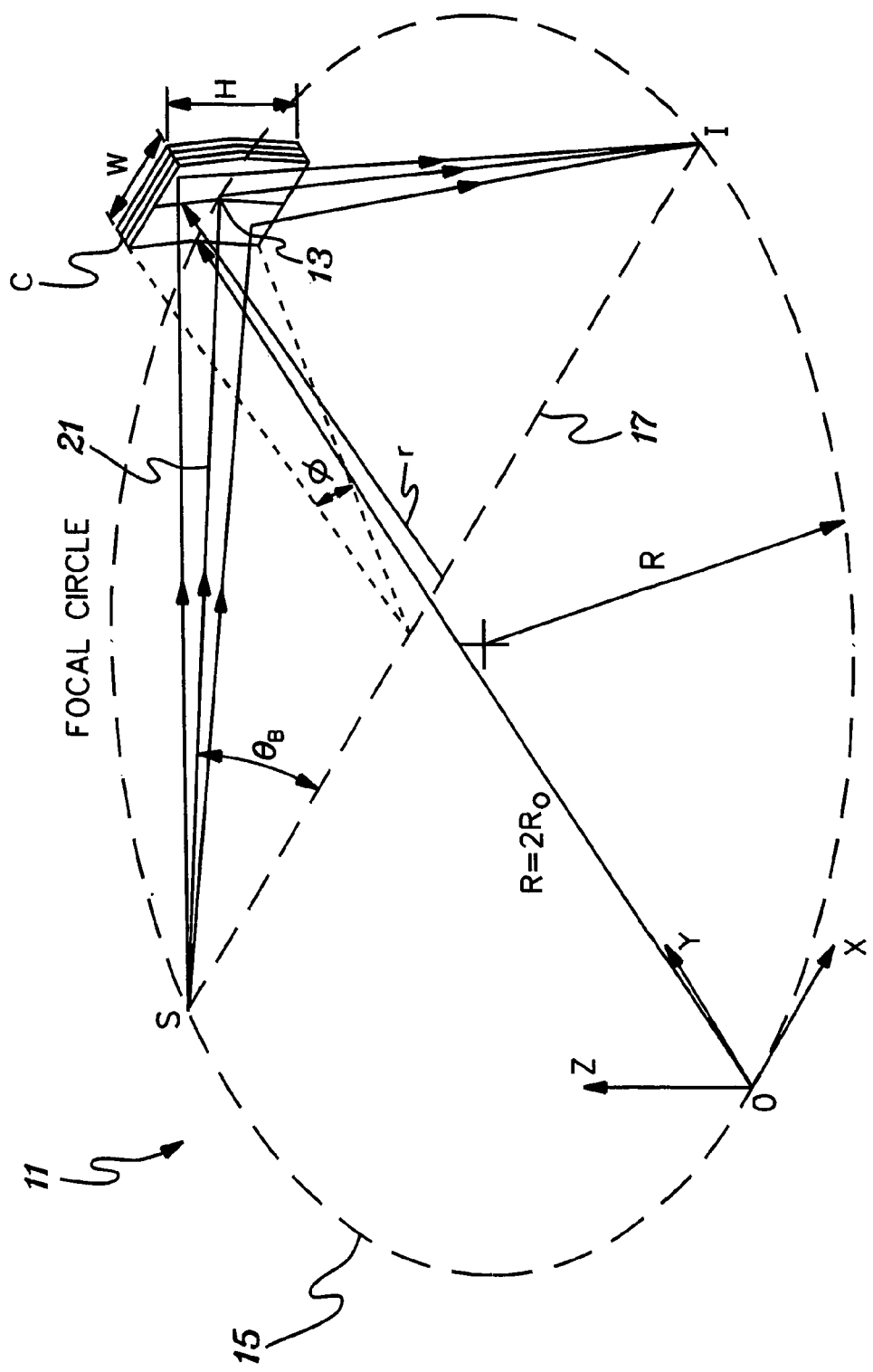
FIG. 2 is a schematic diagram illustrating the geometry of a prior art crystal optic employing Johan-type geometry.

FIG. 2 is a typical isometric view of a prior art x-ray focusing arrangement 11 having doubly-curved crystal (DCC) optic C, an x-ray source location S, and an x-ray target or image location I, at which the x-ray image is preferably produced. X-rays diverging from a point source S, and striking the surface of crystal C with incident angles within the acceptance rocking curve width of the crystal will be reflected efficiently to target location I. In FIG. 2, and in subsequent aspects of the present invention, x-ray source location S represents the point source location for any type of x-rays, for example, source location S may be the point source of a synchrotron, x-ray tube, or any other source of x-rays. Similarly, in FIG. 2 and elsewhere in this specification, target location I may be any target at which x-rays may be directed. For example, target location I may be the location of a chemical specimen undergoing x-ray spectroscopy, human tissue undergoing radiation treatment, or a semiconductor chip undergoing surface analysis, among other things. In addition, the target location I may include an x-ray detector (not shown) for detecting secondary x-rays emitted by the target.

As shown in FIG. 2, the optic crystal C has an optic center point 13, and the x-ray source location S, optic center point 13, and the x-ray target location I define a circle 15 known in the art as the Rowland circle or focal circle. Rowland circle 15 has radius a $R_O$ defined in the art as the Rowland or focal radius. Crystal C has a width W and a height H. X-ray source location S and x-ray target location I are joined by line 17, which is referred to in the art as the "source and image connecting line". The coordinate system of the arrangement shown in FIG. 2 has its origin at the point O.

The surface of crystal C in FIG. 2 has a radius 2R measured from origin O. Crystal C typically contains one or more crystal lattice planes represented by lines 19. In this typical prior art optic, the lattice planes 19 are essentially parallel to the surface of crystal C. Though prior art optics may be designed for Johan or Johansson geometry, the arrangement shown in FIG. 2 has Johan-type geometry in which the radius of curvature R of the surface of crystal C is twice the Rowland radius $R_O$, that is, $R=2R_O$.

As most clearly shown in FIG. 2, prior art crystal C is typically a doubly-curved crystal (DCC), that is, in addition to having a radius of curvature R in the plane of circle 15 (that is, in the Rowland plane), crystal C also has a radius of curvature r in the plane orthogonal to the plane of circle 15. The direction of curvature r is typically referred to in the art as the toroidal curvature of crystal C, and r is referred to as the "toroidal rotation radius". This toroidal direction is indicated by angle $\Phi$ in FIG. 2. In order to provide essentially point-to-point focusing, DCC C typically has a toroidal rotation radius, r, that is equal to the perpendicular distance between crystal center point 13 and source and image connecting line 17.

The angle $\theta_B$ shown in FIG. 2 is known in the art as the "Bragg angle", that is, the critical angle of incidence of the x-ray radiation from source location S upon the surface of crystal C whereby the most radiation is diffracted toward target location I. At angles of incidence larger and smaller than the Bragg angle, less incident radiation is diffracted to the target. The Bragg angle for a system is a function of the crystal used and the frequency of the x-ray radiation used, among other things. In the typical prior art system shown in FIG. 2, system 11 is designed so that the angle of incidence of the x-rays, as indicated by line 21, on center 13 of the surface of crystal C relative to line 17, is equal the Bragg angle for the system. In terms of the Bragg angle, the ideal toroidal curvature r is given by the expression $2R \sin^2 \theta_B$. These terms and dimensions used to define the geometry of the prior art shown in FIG. 2 will be helpful in describing the present invention.

Finite source size, crystal quality, and geometrical aberration affect the focusing properties of a Johann point-focusing crystal. The geometrical aberration is shown to be small for small rocking curve widths or small focal circle radii and it decreases with larger Bragg angles. For a Bragg angle of 23 degrees and R=250 mm, the geometrical aberration is about 1 m. Since the source size of a typical commercial microfocus x-ray tube is in the range of 5 to 100 mm, the dominant broadening effect at the image point will be the x-ray source size.

Figure 3:
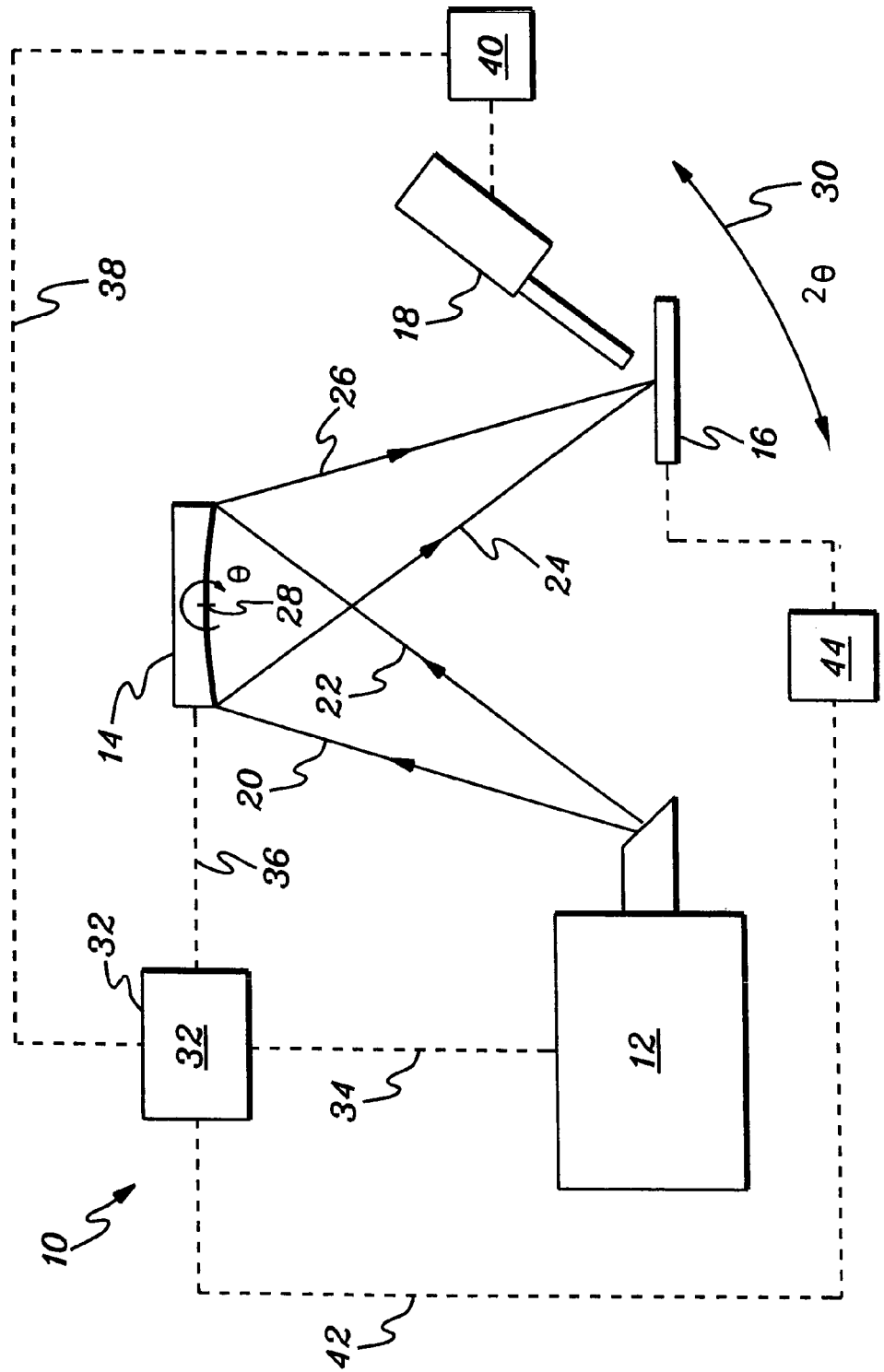
FIG. 3 is schematic diagram of XANES analysis system according to one aspect of the present invention.

FIG. 3 is schematic diagram of a XANES analysis system 10 according one aspect of the present invention. System 10 includes a source of x-rays 12, a crystal optic 14, a sample stage or sample retainer 16, and an x-ray detector 18. Arrows 20 and 22 represent the divergent radiation emitted by source 12 which impinges upon the surface of optic 14. Arrows 24 and 26 represent the convergent radiation diffracted by optic 14 and directed toward the sample under analysis in sample retainer 16. System 10 of FIG. 3 typically complies with the Rowland circle geometry shown in and described with respect to FIG. 2.

X-ray source 12 may be any source of x-rays, but to obtain a reliable XANES spectrum, the x-ray source intensity is preferably very stable or is monitored. In a synchrotron beam line, the intensity of the x-ray beam must be monitored for reliable measurements. However, sealed x-ray microfocus sources have the advantage when applied to the present invention of providing continuous operation with high stability, thus eliminating the need for monitoring the incident beam intensity, and simplifying the system. According to one aspect of the present invention, source of x-rays 12 comprises a sealed micro x-ray source, for example, sealed microfocus x-ray source with a heavy element target, for example, a tungsten target, though other types of targets may be used. In one aspect of the invention, the source of x-rays can be an ultra-bright microfocus x-ray tube sold by Oxford Instruments. Such a tube has a maximum power of about 80 Watts and a source spot size of about 50 microns. The tube is also only about 4.5 inches in diameter, about 17 inches long, and weighs only about 9 pounds. The relatively small size of this x-ray source, allows the present invention to be relatively small and compact compared to prior art systems. According to another aspect of the invention, x-ray source 12 may be a 50 Watt tungsten microfocus source or a 15 Watt Trufocus molybdenum source. According to another aspect of the invention, x-ray source 12 may also be a 4.5 Watt microfocus x-ray tube.

According to the invention, optic crystal 14 captures narrow band x-rays emitted from the bremsstrahlung spectrum from source 12 and focuses the x-rays to a small spot on a sample in sample retainer 16. In one aspect of the invention, optic crystal 14 is one or more curved crystals, for instance, one or more singly-curved optical crystals or doubly-curved optical crystals, for example, one or more toroidal doubly-curved optical crystals. In one aspect of the invention, optical crystal 14 comprises one of the optics disclosed in the above-incorporated U.S. provisional application entitled "An Optical Device for Directing X-Rays having a Plurality of Optical Crystals". According to one aspect of the invention, the x-ray spot size on the sample produced by crystal 14 is very small. The small spot size on the sample that is achievable with one aspect of the present invention, for example, is advantageous when examining individual species in a heterogeneous sample.

In one aspect of the invention, optic crystal 14 of system 10 comprises a doubly-curved silicon crystal optic having 311 diffraction planes. A silicon crystal is preferred over other crystals, for example, germanium crystals, since silicon crystals are flexible and easier to bend, for example, double bend, and can be thinned to thicknesses less than 50 microns quite easily. Specifically, the preferred silicon crystal optical has a major bending diameter (2R) of about 220 mm; a minor bending radius (r) of about 90 mm; a focal distance (f) of about 140 mm; and a Bragg angle ($\theta_B$) of about 40 degrees. This crystal optic typically has a predetermined focusing energy of about 6.0 kilo-electron-Volts and an energy bandwidth resolution of less than about 10 electron-Volts, and can have an energy bandwidth resolution of less than about 5 electron-Volts. For example, when an x-ray beam from a Mo TruFocus 9050 source was directed at this silicon crystal, the crystal produced a 5.99 keV beam energy having a beam flux of $1\times10^5$ photons/second, a beam spot size of 87 microns and an energy bandwidth of 3.5 eV. This crystal can be designed to diffract x-rays at an energy which corresponds to the K-edge of a transition metal, for example, chromium (Cr), copper (Cu), nickel (Ni), or cadmium (Cd). This crystal may be toroidal in shape and produce a focal spot of about 100 microns or less, or even about 85 microns, or less.

The sample retainer or stage 16 may be any type of retainer or stage upon which or within which a sample can be exposed to x-rays. For solid or semi-solid samples, retainer or stage 16 may simply be a surface upon which the sample can be laid. For example, for elements above Si on the Periodic Table, the sample can be exposed to air; for elements below Si on the Periodic Table analysis may require at least some vacuum or an inert gas environment, for instance, a helium environment. For liquid or gaseous samples, retainer 16 may be an open or closed enclosure or container, for example, a plastic dish with a thin propylene window. The samples analyzed may be homogeneous or heterogeneous. The enclosure may contain a window which is transparent to x-rays, for example, a glass or mylar window. For continuous or intermittent analysis of moving fluids, for example liquids or gases, retainer 16 may comprise an inlet and an outlet for introducing and removing a fluid sample. The inlet and outlet may comprise appropriate conduits and flow control means, for example, valves and valve controllers, for instance automated controllers. As will be discussed below, in one aspect of the invention, retainer 16 is moveable or translatable in a linear direction or an angular direction as indicated by double arrow 30.

The x-ray detector 18 may be any type of x-ray detector which can be used to detect the fluorescence signal from the sample, but in one aspect of the invention, x-ray detector 18 is a solid state energy dispersive detector. Since, according to one aspect of the invention, a compact system is provided, solid state energy dispersive detector is preferably very small. In one aspect of the invention, detector 18 is a thermoelectric-cooled Si PIN-type detector manufactured by Amptek, having a 25 square mm detection area, though other similar detectors may be used. This Amptek detector has a body that is only about 1.2 inches by about 2 inches by about 3 inches in size.

The focusing geometry of a curved crystal, for example, a doubly-curved toroidal crystal, is unique for a specific wavelength of x-rays impinging upon it. However, within a narrow window of photon energy, the focusing and reflection properties of a toroidal crystal do not change significantly with small changes in the crystal orientation. Therefore, the x-ray energy can be tuned over a range (typically ~100 eV) by tilting the crystal around an axis perpendicular to the focal plane and passing through the center of the front surface of the optic, as shown in FIG. 3. With x-ray source 12 fixed, a rotation θ of crystal 14 results in a 2θ rotation of the focused beam. To keep the focused beam at the same position on the sample, the sample stage 16 and the fluorescence detector 18 are rotated through an angle of 2θ.

According to one aspect of the present invention, crystal optic 14 is tunable, for example, tunable wherein the energy of x-ray beam 24, 26 can be varied to provide variation in the energy of the x-rays directed toward the sample on sample retainer 16. One means of tuning crystal optic 14 is by scanning crystal optic 14, for example, by rotating optic 14 about an axis 28 perpendicular to the focal circle plane and passing through the center of the optic. For example, as shown in FIG. 3, crystal optic 14 may be rotated about axis 28 as indicated by angular rotation θ. With the x-ray source 12 stationary, the rotation θ about axis 28 will alter the angle of incidence of incident x-rays 20, 22 and as a result the energy of the diffracted x-rays 24, 26 will vary. In order to compensate for this change in orientation and to keep the focused beam on the same location on the sample in the sample retainer 16, in one aspect of the invention, the θ rotation of crystal optic 14 is accompanied by a 2θ rotation of the sample retainer 16 about axis 28, as shown by arrow 30. In order to keep detector 18 in a position to detect secondary x-ray emissions from the sample, in one aspect of the invention, as crystal optic 14 rotates through an angle θ, sample retainer 16 and x-ray detector 18 are rotated through an angle 2θ. This θ-2θ scanning (or tuning) mechanism is a known technique in the art of x-ray diffractometry, but its application to XANES techniques does not appear in the prior art.

According to the present invention, the rotation of crystal optic 14 about axis 28 and the corresponding rotation of sample retainer 16 about axis 28 effectively varies the energy of the x-rays 24, 26 directed on the sample. As a result, according to one aspect of the present invention, the θ-2θ rotations provide the desired energy variation to effect a XANES analysis of a sample in sample retainer 16.

The operation and movement of system 10 may be automated by means of one or more appropriate actuators and controllers, for example, a controller 32. The controllers and actuators may be those provided by Newport Controls. Controller 32 may be a computer, programmable logic controller, or distributed control system, and the like. Controller 32 may provide may provide multiple electronic control signals 34, 36, 38, and 42. These control signals may be carried over IEEE-488 (GPIB) interface bus or an equivalent bus. In one embodiment of the invention, controller 32 provides signal 34 to operate, translate, or rotate x-ray source 12; control signal 36 to translate or rotate crystal 14; control signal 38 to operate an actuator 40 for controlling the operation, translation, or rotation of detector 18; and control signal 42 to an actuator 44 to control the operation, translation, or rotation of sample retainer 16. According to one aspect of the invention, sample retainer 16 and detector 18 are moved in tandem to ensure detector 18 is properly aligned with the sample. Therefore, actuators 40 and 44 may be a single actuator. According to another aspect of the invention, actuator 40 may also comprise a data acquisition system for recording one or more characteristics of the x-ray fluorescence signal detected by detector 18. The data acquisition system may be a Tennelec PCA multiport multichannel analyzer, or its equivalent. Control signal 38 from controller 32 may also control the operation of data acquisition system 40. The operation, control, and movement of the components in system 10, according to another aspect of the invention, may be effected manually.

Experiments were performed according to the present invention using a compact laboratory system similar to the system 10 shown in FIG. 3. In the experimental system, x-ray source 12 comprised a stationary TruFocus Molybdenum x-ray source, crystal 14 comprised a doubly-curved silicon crystal optic having (311) crystal diffraction planes as described above, and detector 18 comprised an Amptek PIN-type detector. The Amptek detector has an active area of 25 mm$^2$ and was placed about 5 mm from the sample on sample retainer 16. In the experimental system, crystal 14, sample retainer 16, and detector 18 were mounted on a compact θ-2θ table, whereby as crystal 14 is rotated about axis 28 through an angle degrees, detector 18 and sample retainer 16 are rotated through an angle 2θ about axis 28.

Three standard samples were analyzed for comparison using the experimental system: (1) a pure chromium (Cr) powder, (2) a solution containing Cr3+ ions ( ); and a solution containing Cr6+ ions ($Na_2CrO_4$). Both the Cr3+ ion concentration and Cr6+ ion concentration were 1000 ppm (that is, 0.1%) aqueous solutions. The Cr powder was spread on an adhesive base and mounted vertically. The Cr3+ and Cr6+ solution were encapsulated in a plastic container with a thin mylar window and was also mounted vertically. The Amptek detector 18 was used to detect the Cr fluorescence signal.

With reference to FIG. 3, the angle at which the incident x-ray photons from the source impinge upon the surface of crystal 14, that is, the surface of doubly-curved Si(311) crystal, determines the energy of the primary beam 24, 26 on the sample in sample retainer 16. According to the present invention, by scanning or varying the angle that the x-ray photons impinge the surface of crystal 14, the beam energy directed toward the sample can be tuned to an energy near the energy of the Cr K absorption edge, that is, about 6.00 keV. In the experimental procedure, XANES spectra were obtained by measuring the fluorescence signal of Cr Kα vs. the incident beam energy for the three samples while varying the angle of incidence of the beam 20, 22 upon crystal 14. In accordance with one aspect of the present invention, the variation in beam energy impinging upon the sample is effected by repeatedly rotating crystal 14 about axis 28, with consequent rotation of sample holder 16 and detector 18 by means of the θ-2θ table. Then exposing the sample to the resulting x-rays from crystal 14, detecting the resulting fluorescent x-rays from the sample using detector 18, recording the energy of the incident and fluorescent x-rays, for example, by means of data acquisition system 40, and repeating the process for subsequent θ-2θ rotations and energies.

For the Cr powder experiments, the measurement time for each data point was about 3 seconds and the whole scan took about 3 minutes. The measurement time for each data point for the Cr ionic solutions were about 180 seconds and the entire scans took about 3 hours. All the measurements were done at a source setting of 18 keV and 0.25 mA, that is, about 4.5 Watts. The maximum power setting for this TruFocus source was about 50 kV 0.3 mA, that is, about 15 Watts. Though not used in these experiments, according to one aspect of the invention, the paths of the x-rays may be shielded to minimize the effects of x-ray scattering that can occur at higher source voltage settings.

Figure 4:
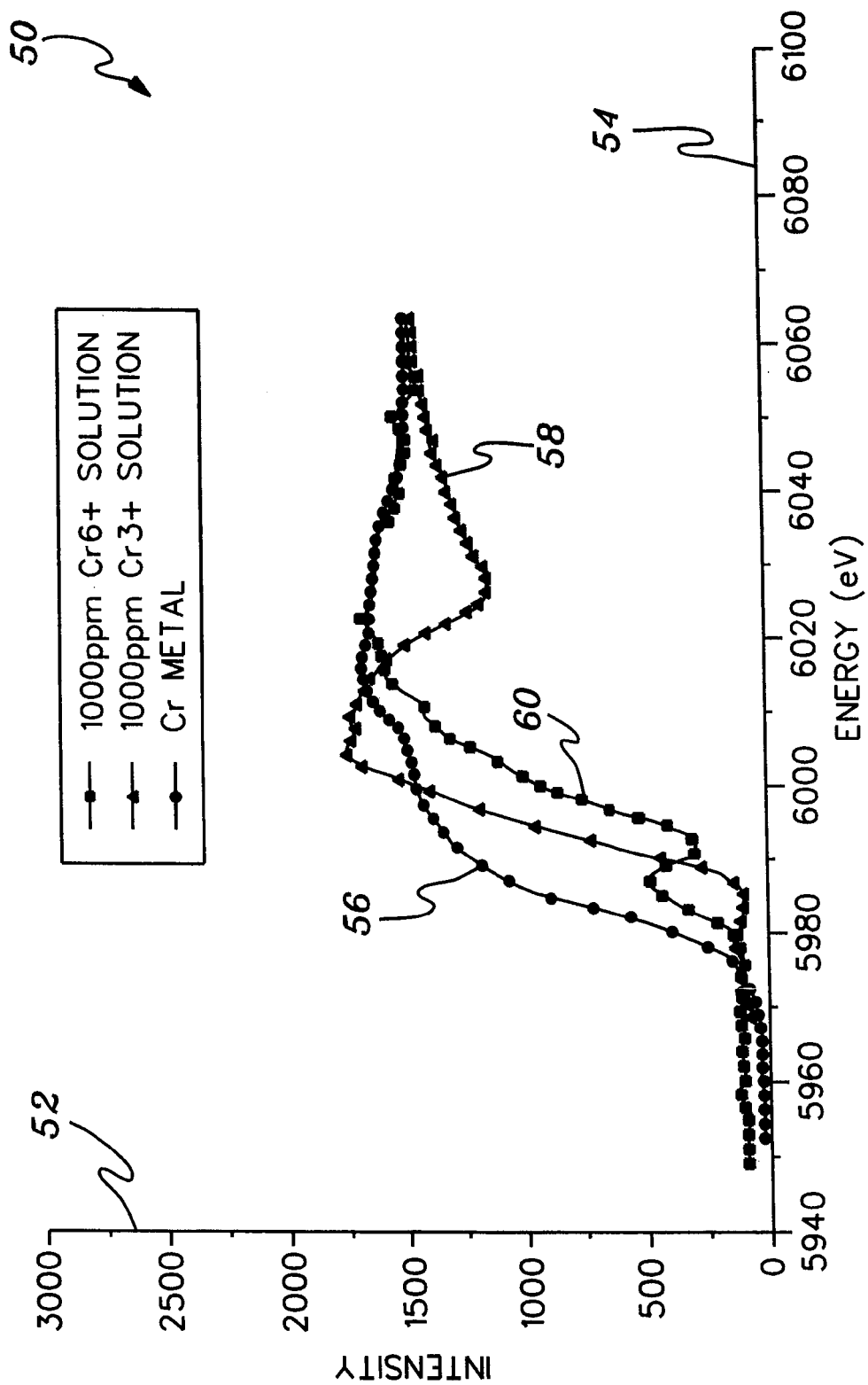
FIG. 4 is a comparison of three typical near-edge x-ray absorption spectra for chromium of different oxidation states obtained using one aspect of the present invention.

The XANES spectra of the three samples examined in this experiment, normalized to the intensity of the x-ray energy 6070 eV, are shown in plot 50 of FIG. 4. In FIG. 4 the ordinate 52 of plot 50 is the intensity of the x-ray fluorescence detected by detector 18. The abscissa 54 of plot 50 is the energy in eV of the corresponding x-ray directed by crystal 14 on the sample in sample retainer 16. Curve 56 in FIG. 4 represents the XANES spectrum for the Cr powder; curve 58 represents the XANES spectrum for the Cr3+ solution; and curve 60 represents the XANES spectrum for the Cr6+ solution. The Cr6+ and the Cr3+ spectra are in good agreement with $CrO_4$ and $Cr_2O_3$ synchrotron-based XANES measurements. An extremely low background was observed in the fluorescence measurement corresponding to a signal-to-noise (S/N) ratio of greater than 10 for a concentration of 10 ppm Cr. According to one aspect of the present invention, spectra such as those shown in FIG. 4 may be calibrated with standard spectra or deconvolution of the spectra can be used to measure mixtures of oxidation states. In addition, the changes in the oxidation states at trace levels of detectability and microscale spatial resolution can be determined.

The XANES analysis system according to one aspect of the present invention provides excellent energy resolution for XANES analysis. The spectra illustrated in FIG. 4 produced according to the present invention clearly different between the three species analyzed. For example, first, the position shift of the absorption sedge for the different oxidation states was clearly observed. The pre-edge feature of Cr6+ can also be seen. Secondly, dilute Cr species in the solution can be identified even with the x-ray source operating at only 4.5 Watts.

It will be apparent to those of skill in the art that the sensitivity and speed of this XANES system according to one aspect of the present invention may be improved several orders of magnitude by using an optimum x-ray source 12 and optimum design of the doubly-curved crystal 14. For example, instead of using an molybdenum (Mo) anode for x-ray source 12, a tungsten (W) anode may be used and a factor of 1.78 times intensity gain may be achieved. In addition, the power loading of the source can also be increased to 50 Watts instead of the 4.5 Watts used in these experiments. Also with an optimum design of the optic, the collection angle and the reflection efficiency can also be improved. It is feasible that a factor of 9× can be achieved for a large aperture doubly-curved crystal, for example, using one of the large aperture doubly-curved crystals disclosed in the above-incorporated U.S. Pat. No. 6,285,506. According to another aspect of the present invention, with these further improvements, among others, the sensitivity of the XANES analysis system according to the present invention may sufficiently improved that sample having element concentrations as low as the lower parts per million (ppm) range or even as low as the parts per billion (ppb) range may be effectively detected and analyzed.

Although the total measurement time for the Cr ionic solution was about 3 hrs, it is apparent to those of skill in the art that much lower measurement times may be achieved using the present invention to identify the XANES edge position shift. For example, since only an energy range of 30 eV to 40 eV is needed for monitoring the change of Cr6+ to Cr3+, for example when investigating the change of these ions in cells, the total experimental measuring time may be much less than 3 hours, for example, only one hour may be needed, or even only 30 minutes, or less. In addition, the scanning time may be further reduced with the use of higher intensity x-ray beams. According to one aspect of the invention, the measurement time for a XANES analysis, for example, a XANES analysis to monitor the changing of Cr6+ to Cr3+ in cells, the measurement time may be reduced to 10 minutes or less, 1 minute or less, or even 1 second or less, and detection sensitivity lowered to low ppm concentration levels.

Though the experiments outlined above investigated the XANES spectra for chromium (Cr), it will be apparent to those of skill in the art that XANES spectra for any other elements having characterizing near-edge absorption spectra may be obtained using the methods and apparatus of the present invention. For example, the methods and apparatus of the present invention may be used to determine XANES spectra for any transition element, for example, copper (Cu), nickel (Ni), cadmium (Cd), titanium (Ti), vanadium (Va), manganese (Mn), tellurium (Te), rhenium (Re), among others.

Figures 5, 6:
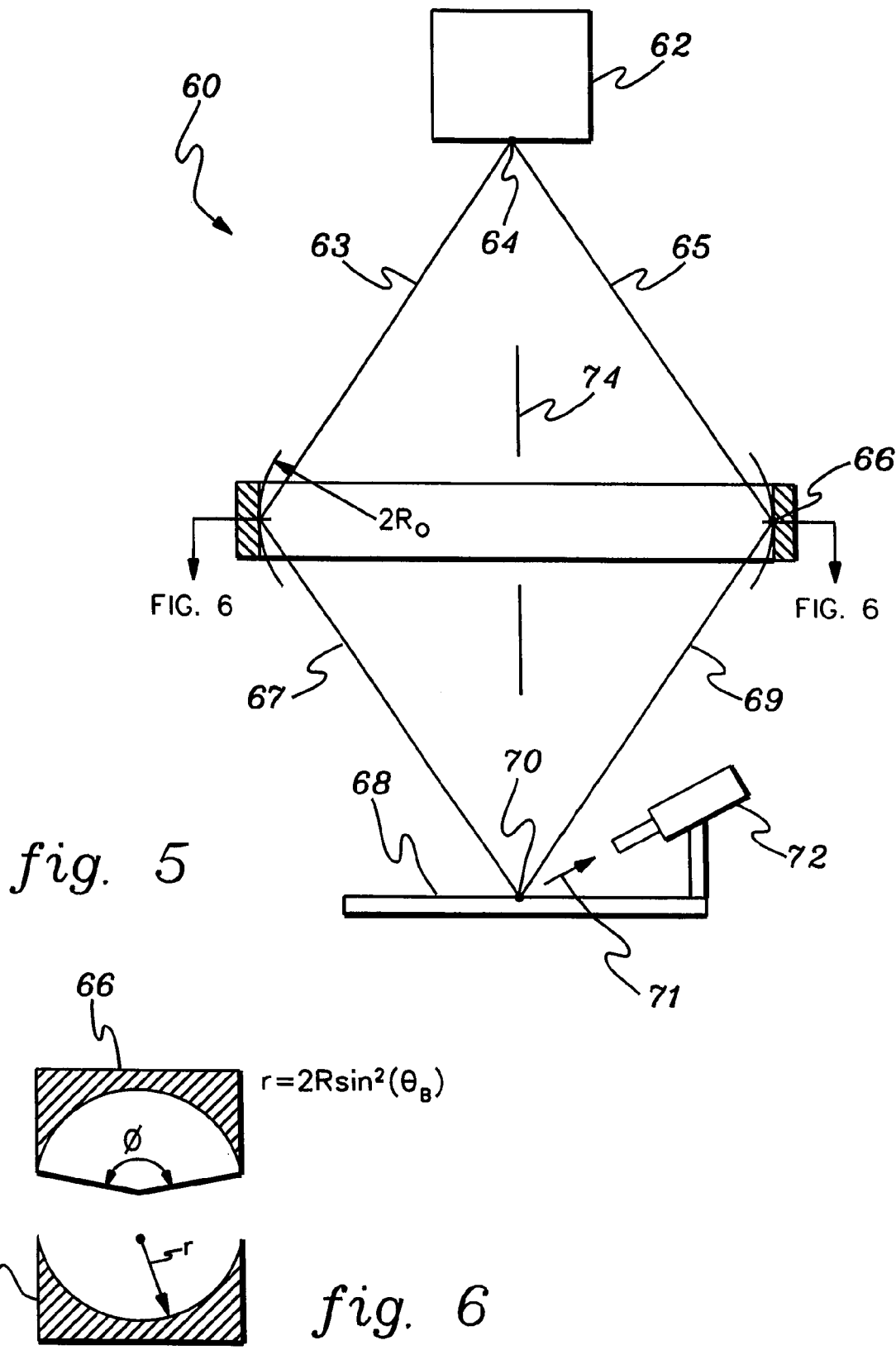
FIG. 5 is a schematic diagram of a compact XANES analysis system according to another aspect of the present invention.
FIG. 6 is a section view taken through the view lines 6—6 shown in FIG. 5.

FIG. 5 illustrates a further aspect of the present invention. FIG. 5 illustrates a XANES analysis system 60 comprising a x-ray source 62, having a source spot 64; an x-ray optic 66 (shown in cross-section); a sample holder 68, on which a target spot 70 is produced; and an x-ray detector 72. Lines 63, 65 define the edges of the cone of the x-ray emitted by source 62 which impinge the surface of optic 66; lines 67, 69 define the edges of the cone of the x-ray beam directed by optic 66 toward the sample in sample holder 68. According to one aspect of the present invention, optic 66 captures narrow-band x-rays from the bremsstrahlung spectrum emitted by x-ray source 62 and directs the x-rays, for example, focuses the x-rays, to a small spot on a sample in sample holder 68. The optical axis of system 60, that is, the line connecting the center of the source spot 64 and the focal target spot 70, is shown by line 74.

According to one aspect of the invention, x-ray optic 66 comprises a large-aperture x-ray optic. A cross-section of optic 66 viewed through section lines 6—6 in FIG. 5 is shown in FIG. 6. Unlike optic 14 shown in and described with respect to FIG. 3, which typically has an azimuthal angle, $\Phi$ (see FIG. 2), of about 30 degrees to about 40 degrees, for example, 36 degrees, in one aspect of the present invention, as shown in FIG. 6, large-aperture optic 66 may have an azimuthal angle $\Phi$ greater than about 45 degrees. Optic 66 has a radius of curvature in the Rowland circle plane of twice the radius of the Rowland circle radius $R_O$. In one aspect of the invention, the azimuthal angle of optic 66 is greater than about 90 degrees, and may be greater than about 180 degrees. For example, in the embodiment shown in FIG. 5, optic 66 may comprise an azimuthal angle $\Phi$ of about 360 degrees, that is, optic 66 may comprise a complete circle. As shown in FIG. 6, in one aspect of the invention, the toroidal radius r of optic 66 is equal to $2 R_O \sin^2(\theta_B)$. In one aspect of the present invention, optic 60 comprises one of the optics disclosed in the above-incorporated U.S. provisional application entitled "An Optical Device for Directing X-Rays Having a Plurality of Optical Crystals."

Increasing the azimuthal angle of a crystal optic will increase the primary beam intensity of the x-rays directed to the target 70, for example, increasing the azimuthal angle of optic 14 in FIG. 3 from about 36 degrees to about 180 degrees can increase the intensity by a factor of about 5, while increasing the azimuth angle to about 360 degrees can increases the intensity by a factor of about 10. As disclosed in the above-references co-pending provisional application 60/400,809, an single optical crystal having an azimuthal angle greater about 45 or a mosaic, or matrix, or plurality, of optical crystals with an azimuthal angle greater than 45 degrees, for example, having an azimuthal angle of about 180 degrees or 360 degrees, can be fabricated. Though in one aspect of the invention, a single-piece crystal optic having an azimuthal angle of about 360 can be used, in another aspect of the invention, two or more optics, for example, comprising toroidal optical crystals, each having an azimuthal angle less than 360 degrees, may be used. For example, each optic may have an azimuthal angle of about 45 degrees, or about 90 degrees, or about 120 degrees, or about 180 degrees, or any other azimuthal angle, and the one or more optics may be assembled to provide the desired azimuthal angle for the optic assembly, that is, an optic assembly having the an optimum x-ray beam capture angle.

X-ray source 62 may be any x-ray source, for example, x-ray source 62 may be similar to x-ray source 12 shown in FIG. 3. However, according to one aspect of the present invention, x-ray source 62 comprises a sealed micro x-ray source, for example, a compact microfocus tube with tungsten (W) target developed by Varian Medical Systems of Salt Lake City, Utah. A typical x-ray tube provided by Varian can be about 4 inches in diameter and about 6 inches long and weigh only about 2 pounds. According to one aspect of the invention, x-ray source 12 comprises an x-ray tube having a maximum power of about 50 Watts and a source spot size of about 100 microns. According to another aspect of the invention, in which a large-aperture optic 66 is used, x-ray source 62 provides an x-ray cone angle that is greater than the cone angle of conventional x-ray sources. For example, in one aspect of the invention, the cone angle of x-ray source 62 is greater than about 30 degrees, and may be greater than about 60 degrees, and even greater than about 90 degrees. In one aspect of the invention the cone angle of x-ray source 62 is greater than the Bragg angle of the optic 66 being used in system 60, for example, about twice the Bragg angle of large-aperture optic 66. For example, in one aspect of the invention optic 66 comprises the Si(311) doubly-curved toroidal crystal described above having a Bragg angle of about 39 degrees for producing an x-ray beam having an energy of 6 keV and having an azimuthal angle of about 360 degrees. According to this aspect of the invention, x-ray source 62 would preferably have a cone angle of about twice 39 degrees, or about 78 degrees, to fully utilize the diffraction capability of the 360 degree optic. According to one aspect of the invention, x-ray source 62 having a cone angle less than twice the Bragg angle of the optic 66 may be used; however, such x-ray sources would not utilize the full potential of optic 66. In one aspect of the invention, the x-ray source spot size comprises a spot size less than 100 microns, and may be less than 50 microns.

According to one aspect of the invention x-ray source 62 may be a TruFocus brand commercial series x-ray tube manufactured by Oxford Instruments of Scotts Valley, Calif., and having model number 8050 and a power rating of about 15 Watts. According to another aspect of the invention, source 62 comprises an Oxford 5011 series x-ray tube which can operate at about 50 Watts and provide a source spot size of less than about 100 microns and a cone angle of about 26 degrees.

Sample holder 68 may be any conventional means for retaining a sample for analysis, for example, retainer 16 shown in and described with respect to FIG. 3.

Detector 72 may also be any type of appropriate x-ray detector which can detect the fluorescence x-rays emitted from a sample, for example, a detector similar to detector 18 shown in and described with respect to FIG. 3. According to one aspect of the invention, detector 72 comprises a small energy-dispersive detector, for example, a solid-state energy dispersive detector. According to one aspect of the invention, detector 72 comprises a compact thermoelectric cooled Si PIN-type detector, for example, one manufactured by Amptek or Moxtek. This detector typically has a body of only about 1.2 inches×about 2 inches×about 3 inches in size. These detectors typically have an energy resolution of about 300 eV or less and active detector areas of about 25 square mm or less.

In one aspect of the invention, the signal detected by detector 72 is forwarded to, stored, and analyzed by an appropriate data acquisition system, for example, a data acquisition system similar to the system 40 used for system 10 shown in and described with respect to FIG. 3.

Though the components of system 60 in FIG. 5 are shown arranged in a vertical orientation, the present invention is not limited to this vertical orientation of system 60. The components of system 60 may arranged in any compatible orientation, including horizontally, as long as the components can interact as desired.

Similar to system 10 in FIG. 3, according to one aspect of the present invention, the energy of x-ray beam directed by optic 66 upon the sample retained in sample holder 68 in FIG. 5 is variable, for example, to provide a varying x-ray energy to effect XANES analysis. Again, similar to system 10 of FIG. 3, the desired variation of the energy impinged upon the sample is effected by "tuning" the optic, that is, by varying the angle of the x-rays incident on the doubly-curved crystal optic 66. However, due to the linear orientation of the components of system 60 in FIG. 5 and the desire to fully utilize the large-aperture of optic 66, θ-2θ tuning of system 10 of FIG. 3 does not apply to system 60 of FIG. 5. Instead, according to one aspect of the present invention, the tuning of system 60 is effected by a linear translation of one or more of the components in system 60.

Figure 7:
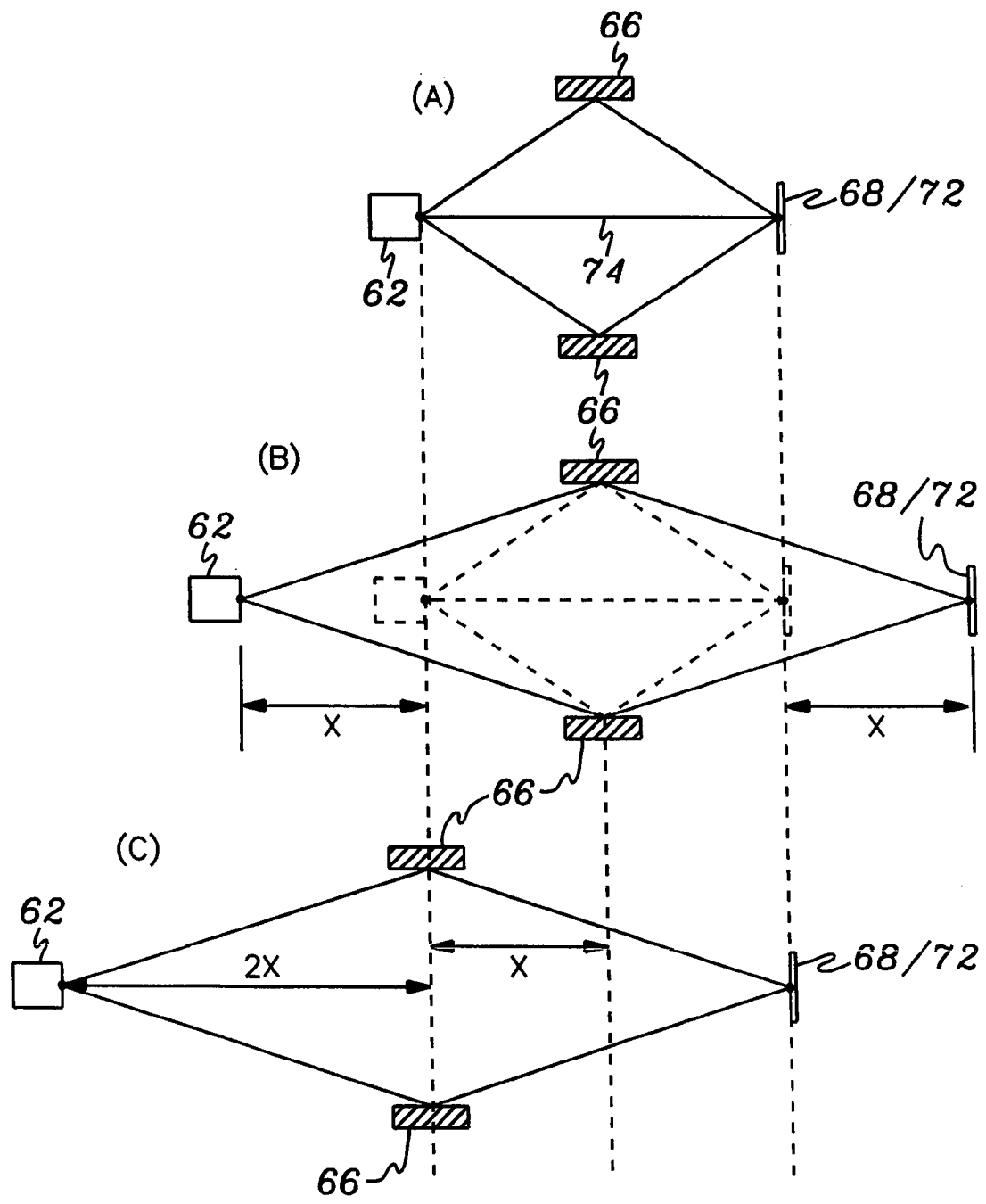
FIGS. 7A, 7B, and 7C are schematic diagrams of tuning options for a XANES analysis system according to one aspect of the present invention.

The tuning of system 60 is summarized in FIGS. 7A, 7B, and 7C. FIG. 7A illustrates the baseline or original position of source 62, optic 66, target 68, and detector 72, for example, as shown in FIG. 5. FIG. 7B illustrates one aspect of the invention in which the position of optic 66 is fixed and the location of source 62, sample holder 68, and detector 72 are varied. For the sake of simplifying the discussion, sample holder 68 and detector 72 are assumed to move together as a single component. In one aspect of the invention shown in FIG. 7A, system 60 is tuned by varying the angle of incidence of the x-rays emitted by source 62 upon optic 66. This tuning is effected by translating source 62 along the optical axis 74 a distance x. Typically, according to this aspect of the invention, to ensure proper focusing of the diffracted x-rays from optic 66 to the sample in sample holder 68, sample holder 68 and detector 72 are also moved along the same axis 74 about the same distance x, but in the opposite direction. For example, with the position of optic 66 held constant, in order to ensure proper directing of x-rays upon the sample in sample holder 68, moving the source 62 away from the optic 66 a distance x (which decreases the incident angle of the x-rays on optic 66) requires moving the sample holder 68 away from optic 66 a distance about equal to x. According to another aspect of the present invention, as source 62 moves toward the crystal 66 a distance x, which increases the incident angle of x-rays on the optic 66, the sample holder 68 is moved toward optic 66 a distance about equal to x, preferably in a synchronized way, to maintain the desired focusing geometry. According to this aspect of the invention, this is referred to as "x-x tuning". That is, the translation of the source 62 a distance "x" requires a corresponding translation of sample holder 68 a distance "x", but in a direction opposite the translation of source 62.

In an alternative aspect of the invention shown in FIG. 7C, sample holder 68 and detector 72 are held stationary (relative to their respective positions in FIG. 7A) and the desired variation in angle of the incident x-rays on optic 66 is effected by translating optic 66 along optical axis 74 a distance x either toward or away from sample holder 68. According to this aspect of the invention, in order to maintain proper focusing on the sample in sample holder 68, source 62 is translated a distance 2x in the same direction as the translation of optic 66 along axis 74. According to this aspect of the invention, this translating is referred to as "x-2x tuning". As discussed with respect to system 10 in FIG. 3 the translation and tuning of system 60 of FIGS. 7A, 7B, and 7C may be effected by means of automated actuators and controllers.

Figure 8:
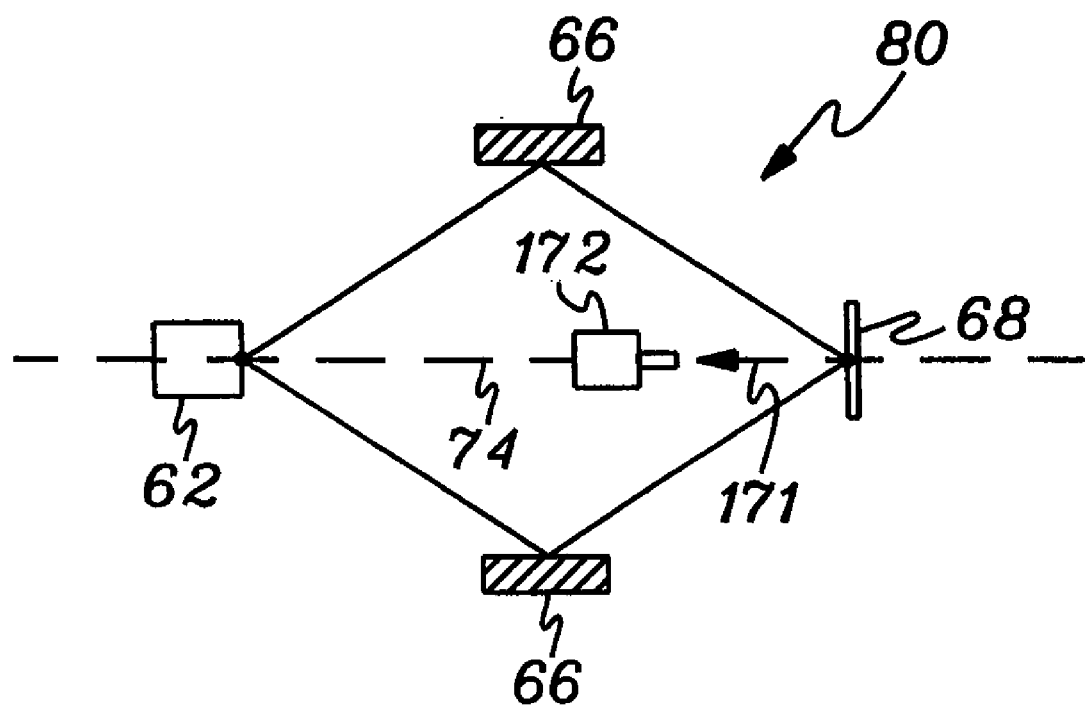
FIG. 8 is a schematic view of a compact XANES analysis system according to another aspect of the present invention.

A further aspect the present invention is illustrated in FIG. 8. In this aspect of the invention, a focusing system 80 includes a source 62, optic 66, and sample holder 68 having a similar linear relationship, for example, positioned collinear to an optic axis 74, as illustrated in FIGS. 5, 7A, 7B, and 7C. However, unlike earlier aspects of the invention, in system 80, includes a detector 172 positioned directly above the sample in sample holder 68 and receives fluorescent x-rays from the sample as indicated by arrow 171. Detector 172 may be similar to detector 72 shown in and described with respect to FIG. 5. In one aspect of the invention, detector 172 is located on the optic axis 74. In another aspect of the invention, detector 172 is positioned off of axis 74 but within the inside diameter of optic 66. The aspect of the invention illustrated in FIG. 8 provides further opportunity to reduce the size or over-all envelope of a focusing system. According to this aspect of the invention, a compact, low power XANES analysis system is provided which is easily tunable by translating one or more of the components and can be used, for example, for laboratory-scale analysis.

The various aspects of the present invention provide methods and systems for implementing XANES analysis. The methods and systems according to the present invention are compact, inexpensive, and low-energy consuming, among other things, compared to prior art XANES systems. The methods and systems according to one aspect of the present invention are ideal for laboratory-scale analysis or field analysis that heretofore was feasible. The methods and systems according to some aspects of the present invention also allow for rapid analysis and on-line analysis of chemical species for use biological sciences, medical sciences, environmental sciences, mineralogy, material sciences, and industrial applications for analysis, research, and process control, among other applications.

While the invention has been particularly shown and described with reference to preferred embodiment, it will be understood by those skilled in the art that various changes in form and details may be made to the invention without departing from the spirit and scope of the invention described in the following claims.

The invention claimed is:

1. A system for performing x-ray absorption near-edge structure analysis, the system comprising:
   a focusing, doubly-curved x-ray optic for directing x-rays having a first energy onto a sample;
   a detector for detecting x-rays having a second energy emitted by the sample when the sample is exposed to x-rays;
   means for varying the first energy of the x-rays directed onto the sample wherein the second energy of the x-rays emitted by the sample varies responsive thereto; and means for analyzing the variation in the second energy of the detected x-rays to provide information concerning near-edge structure of an x-ray absorption spectrum of the sample.

2. The system as recited in claim 1, wherein the x-ray optic comprises a point focusing, doubly curved x-ray optic.

3. The system as recited in claim 2, wherein the x-ray optic comprises a tunable x-ray optic and wherein the means for varying the first energy of the x-rays directed on the sample comprises means for tuning the tunable x-ray optic.

4. The system as recited in claim 3, wherein tuning the x-ray optic comprises θ-2θ tuning.

5. The system as recited in claim 3, wherein tuning the x-ray optic comprises x-x tuning, or x-2x tuning.

6. The system as recited in claim 3, wherein the tunable x-ray optic has an axis, and tuning the x-ray optic comprises means for rotating the tunable x-ray optic about the axis.

7. The system as recited in claim 3, wherein the tunable x-ray optic comprises a crystal optic.

8. The system as recited in claim 7, wherein the first energy of the x-rays directed onto the sample by the crystal optic has a predetermined diffraction energy bandwidth.

9. The system as recited in claim 8, wherein the predetermined diffraction energy bandwidth has a resolution of less than about 10 electron-Volts.

10. The system as recited in claim 2, wherein the x-ray optic comprises a silicon crystal optic having 311 diffraction planes;
    wherein the silicon crystal comprises:
    a major bending diameter (2R) of about 220 mm;
    a minor bending radius (r) of about 90 mm;
    a focal distance (f) of about 140 mm; and
    a Bragg angle ($\theta_B$) of about 40 degrees.

11. The system as recited in claim 10, wherein the silicon crystal optic directs a predetermined focusing energy of about 6.0 kilo-electron-Volts onto the sample.

12. The system as recited in claim 11, wherein the silicon crystal optic produces a focal spot having its largest dimension less than about 100 microns on the sample.

13. The system as recited in claim 2, further comprising a microfocus x-ray source for producing the x-rays.

14. The system as recited in claim 13, wherein the microfocus x-ray source is a sealed microfocus x-ray tube having a heavy element target.

15. The system as recited in claim 13, wherein the microfocus x-ray source consumes less than about 80 Watts.

16. The system as recited in claim 1, wherein the sample contains an element comprising one of chromium (Cr), copper (Cu), nickel (Ni), and cadmium, and the information concerning near-edge structure of an x-ray absorption spectrum comprises information concerning near-edge structure of an x-ray absorption spectrum for the element.

17. The system as recited in claim 1, wherein the means for directing x-rays having a first energy comprises an x-ray optic having an azimuth angle greater than about 90 degrees.

18. The system as recited in claim 17, further comprising an x-ray source and wherein the means for varying the first energy of the x-rays comprises means for varying the location of the x-ray source relative to the location of the x-ray optic.

19. The system as recited in claim 18, wherein the system comprises an optical axis and wherein the means for varying the location of the x-ray source relative to the location of the x-ray optic comprises means for translating the x-ray source along the optical axis.

20. A method of practicing x-ray absorption near-edge structure analysis, the method comprising:
   directing x-rays having a first energy onto a sample using a focusing, doubly-curved x-ray optic;
   detecting x-rays having a second energy emitted by the sample when the sample is exposed to x-rays;
   varying the first energy of the x-rays directed onto the sample wherein the second energy of the x-rays emitted by the sample varies responsive thereto; and
   analyzing the variation in the second energy of the detected x-rays to provide information concerning near-edge structure of an x-ray absorption spectrum of the sample.

21. The method as recited in claim 20, wherein the x-ray optic is a point focusing, doubly curved x-ray optic.

22. The method as recited in claim 21, wherein the x-ray optic is a tunable x-ray optic and wherein varying the first energy of the x-rays comprises tuning the x-ray optic.

23. The method as recited in claim 22, wherein tuning the x-ray optic comprises $\theta$-$2\theta$ tuning.

24. The method as recited in claim 22, wherein tuning the x-ray optic comprises x-x tuning, or x-2x tuning.

25. The method as recited claim 22, wherein the tunable x-ray optic has an axis, and tuning the x-ray optic comprises rotating the tunable x-ray optic about the axis.

26. The method as recited in claim 21, wherein directing x-rays comprises providing a source of x-rays which comprises a microfocus x-ray source.

27. The method as recited in claim 26, wherein directing x-rays comprises providing a source of x-rays which consumes less than about 80 Watts.

28. The method as recited claim 20, wherein directing x-rays having a first energy comprises providing a source of x-rays and providing an x-ray optic for diffracting x-rays and wherein varying the first energy of the x-rays comprises varying the location of the source of x-rays relative to the x-ray optic.

29. The method as recited claim 28, wherein the source of x-rays and the x-ray optic comprise an optical axis, and wherein varying the location of the source of x-rays relative to the x-ray optic comprises translating the source of x-rays along the optical axis.

30. The method as recited in claim 20, wherein the method is practiced in less than about 1 hour.

31. The method as recited in claim 30, wherein the method is practiced in less than about 30 minutes.

* * * * *